United States Patent [19]

LeVeen et al.

[11] 4,346,708
[45] Aug. 31, 1982

[54] SYRINGE

[76] Inventors: Harry H. LeVeen, 321 Confederate Cir., Charleston, S.C. 29407; Robert F. LeVeen, 312 Lombard St., Philadelphia, Pa. 19147; Eric G. LeVeen, 3-3 Woodlike Rd., Albany, N.Y. 12203

[21] Appl. No.: 255,353

[22] Filed: Apr. 20, 1981

[51] Int. Cl.³ .............................................. A61M 1/00
[52] U.S. Cl. ..................................... 128/236; 128/215
[58] Field of Search ............... 128/236, 234, 215, 216, 128/218 R, 218 P, 218 PA, 218 F, 218 C, 220, 348, 349 BV

[56] References Cited

U.S. PATENT DOCUMENTS 3,905,521  9/1975  Mead et al. ................. 128/218 PA
4,064,879 12/1977  Leibinsohn .................. 128/218 P X
4,074,714  2/1978  Binard et al. ..................... 128/218 P Primary Examiner—John D. Yasko
Attorney, Agent, or Firm—Brooks, Haidt, Haffner & Delahunty

[57] ABSTRACT

A syringe comprising a cylindrical barrel with a wall at one end with a nozzle and with a threaded actuating rod extending from its other end, the rod having an axial bore and a piston in fluid tight engagement with the inner wall of the barrel is connected to the rod by compressible spring means which is an extension of the rod threads. The rod also carries a collar with threads which mate with the rod threads, and the collar has slots which engage projections on the barrel and prevent movement of the collar relative to the barrel but which permit the collar to be disengaged readily from the barrel. An indicator rod is connected at one end to the piston and is slidable in the bore of the actuating rod. The opposite end of the indicator rod, bearing graduation marks, extends axially outwardly of the actuating rod. Rotation of the actuating rod causes movement of the piston axially of the barrel when the collar is engaged, and as the pressure on fluid within the barrel increases, the spring means compresses causing the indicator rod to extend farther outwardly of the actuating rod and thereby, indicates the fluid pressure.

8 Claims, 4 Drawing Figures

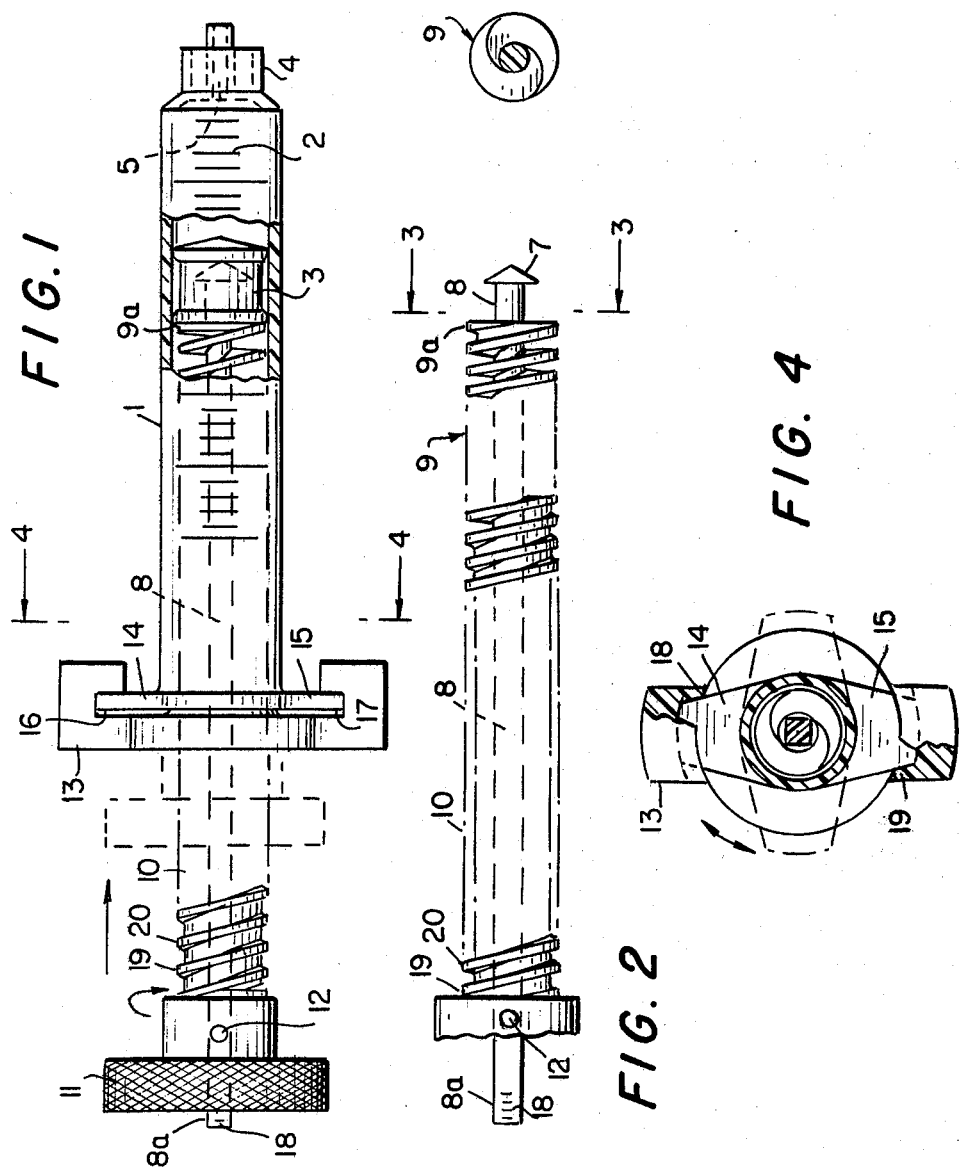

SYRINGE

This invention relates to a syringe for precisely dispensing fluids against relatively high fluid resistance and particularly, to a syringe of such type which has means for indicating the pressure applied to the fluid being dispensed.

Related applications are co-pending Application Ser. No. 061,642, filed July 30, 1979, in the names of two of the inventors named herein and entitled "Syringe" and co-pending application Ser. No. 255,352, filed concurrently herewith, in the names of the inventors named herein and entitled "Syringe".

Syringes are well known in the medical art and are commonly used to supply a fluid to a vein or body cavity or to a device, such as an arterial embolectomy catheter or a tracheal balloon. In some such applications, it is desirable to be able to know the pressure which is being applied to the fluid by the syringe.

Such syringes usually include a hollow cylinder or barrel with an opening or nozzle at one end and a piston or plunger therein which is slidably reciprocable within the cylinder by means of a manually engageable rod or shaft extending from the opposite end of the cylinder. The piston has fluid tight engagement with the inner wall of the cylinder so that as the piston is moved toward the nozzle, fluid can be ejected from the nozzle. The nozzle can be connected to a needle, a catheter or other device.

Said co-pending application Ser. No. 061,642 describes a syringe which overcomes problems of prior art syringes in which the piston and its actuator are manually reciprocated. The syringe comprises a hollow cylinder with a wall at one end having an opening through which the fluid is transported. The opposite end of the hollow cylinder is open and receives a piston rotatably mounted on one end of a threaded rod having a knurled knob at its opposite end. The rod carries a collar having a threaded portion which mates with the thread on the rod. The opposite end of the cylinder has a pair of projections which interfit with a portion of the collar so that after the cylinder is partially filled with the fluid to be transported and the piston is in the cylinder, the collar can be rotated on the rod until it engages the projections which prevents further movement of the collar axially of the cylinder. When the rod is thereafter rotated by means of the knob, the piston moves axially of the cylinder to dispense the fluid through the opening in the end wall thereof. The present invention will be described as applied to a syringe of the type disclosed in said application.

One object of the invention is to provide a self-contained syringe which permits the delivery of fluid under pressure through the syringe opening and which includes means thereon which indicates the pressure being applied to the fluid by the piston of the syringe.

Another object of the invention is to provide such a syringe which may be quickly and easily filled with the fluid to be transported through the syringe opening.

It also is an object of the invention to provide such a syringe which is of such simple construction and economical manufacture that it can be dispensed in a sterile package and be disposed of after use.

In accordance with the preferred embodiment of the invention, the syringe comprises a hollow cylinder with a wall at one end having an opening through which the fluid passes. The opposite end of the hollow cylinder is open and receives a piston rotatably mounted on one end of a threaded rod with an axial bore and having a knurled knob at its opposite end. For reasons explained hereinafter, the threaded on the rod are at least two, parallel, spaced threads, sometimes called "multiple flight" threads and at the portion of the rod nearer the piston, the threads are unconnected at their minor diameters so that the threads at such portion form intercalated, spiral springs acting between the piston and the remainder of the rod. As in said application Ser. No. 061,642, the rod carries a collar having a threaded portion which mates with the threads on the rod. The opposite end of the cylinder has a pair of projections which interfit with a portion of the collar so that after the cylinder is partially filled with the fluid to be expelled therefrom and the piston is inserted in the cylinder, the collar can be rotated until it engages the projections, at which time further movement of the collar axially of the cylinder is prevented. When the rod is thereafter rotated by means of the knob, the piston moves axially of the cylinder to expel the fluid through the opening in the end wall thereof.

The preferred embodiment of the invention also includes an indicator rod slidable in said bore of the threaded rod which, at one end, extends outwardly of the knob and which is marked with indicia. The opposite end of the indicator rod is secured for movement with the piston so that the length of the indicator rod extending outwardly of the knob depends upon the position of the piston in the cylinder and the compression of the thread-springs and hence, the pressure applied to the fluid in the cylinder.

Other objects and advantages of the present invention will be apparent from the following detailed description of the presently preferred embodiments thereof, which description should be considered in conjunction with the accompanying drawing in which:

FIG. 1 is a side view, partly in section, of the preferred embodiment of the invention;

FIG. 2 is a fragmentary side view of the threaded rod and the indicator rod forming part of the preferred embodiment, shown in FIG. 1;

FIG. 3 is a cross-sectional view of the parts shown in FIG. 2 and is taken along the line 3—3 indicated in FIG. 2; and FIG. 4 is a cross-sectional view of the preferred embodiment shown in FIG. 1 and is taken along the line 4—4 indicated in FIG. 1.

The syringe illustrated in the figures of the drawing comprises a cylinder 1 made of a transparent or semi-transparent plastic material permitting visual observation of the contents therein. Graduations 2 are provided on the outer surface of the cylinder 1 to permit measurement of the movement of the piston 3 and hence, of the volume of fluid transported through the nozzle 4 having an opening 5 and surrounded by a sleeve 6 having internal threads for attaching other devices, such as a catheter valve or other device, to the syringe. The piston 3 fits snugly within the bore of the cylinder 1 to provide a fluid tight engagement with the interior wall thereof and is made of a resilient material, such as neoprene rubber. The piston 3 is formed internally so that it snaps over an enlarged portion 7 of an extension of an indicator rod 8.

The indicator rod 8 moves with the piston 3 and is secured in fixed relation to an end 9a of spring means 9 which, at its opposite end, is secured to one end of a manually rotatable, threaded rod 10. Preferably, the spring means 9 is an extension of the threads on the rod 10 so as to provide spiral resilient spring turns which are free to move with respect to each other in the direction axially of the rod 10. Such turns can be provided by omitting or removing the material at the minor diameter of and intermediate the threads. The minor diameter of the turns is slightly larger than the outer diameter of the rod 8 so that the rod 8 can move axially with respect to the turns. The portion of the indicator rod 8 within the spring means 9, and the rod 8 can be square, circular or any other desired shape in crosssection.

The rod 10 extends from the end of the cylinder 1 oposite the end thereof having the nozzle 4 and the opening 5 and has a knurled knob 11 at the end thereof opposite the end of the rod 10 which carries the piston 3. The knob 11 can be integral with the rod 10 or can be secured thereto, such as by means of a pin 12. Preferably, the rod 10, the knob 11, the indicator rod 8 and the spring means 9 are molded from a plastic material, such as an acetal polymer.

The rod 10 carries a collar 13, which can be made of the same material as the rod 10, and which has a threaded bore, the threads of which mate with the threads on the rod 10. Preferably, the fit on the threads is such that when the collar 12 is disengaged from projections 14 and 15 on the cylinder 1, the collar 12 can be spun to permit rapid adjustment of the collar 12 in the axial direction of the rod 10.

The projections 14 and 15 on the cylinder 1 and slots 16 and 17 in the collar 12 form co-operating and interengaging means for releasably securing the collar 12 to the cylinder 1. The diameter of the projections 14 and 15 preferably is slightly larger than the internal diameter of the slots 16 and 17, or the axial dimensions of the slots 16 and 17 preferably are slightly less than the axial dimensions of the projections 14 and 15, or both, so that when the projections 14 and 15 are in the slots 16 and 17 the friction therebetween will prevent rotation of the collar 12 with rotation of the rod 10. In addition, the ends of the slots 16 and 17 can be blocked or partly blocked, such as at 18 and 19 (FIG. 4), by means, such as material of the collar or pins, so that rotation of the collar 12 within the slots 16 and 17 is limited to one direction. However, the collar 12 and the projections 14 and 15 are shaped as indicated in the drawings, and the dimensions of the slots 16 and 17 and the projections 14 and 15 are such, that the collar 12 can be disengaged from the cylinder 1 by manually rotating the collar 12 by one-quarter of a turn with respect to the cylinder 1. When so released, the rod 10 and the piston 3 can be inserted in, or removed from, the cylinder 1 by movement of the rod 10 axially of the cylinder 1 and without rotation of the rod 10.

The rod 10 has an axial bore which extends from one end to the other thereof and the size of such bore is such that the indicator rod 8 can freely move axially of the rod 10. The length of the rod 8 is such that when the spring means 9 is not compressed, a portion 8a of the rod 8 extends outwardly from the knob 11 so that graduation marks 18 thereon are visible. When the spring means 9 is compressed, as described hereinafter, the rod 8 moves to the left, as viewed in FIG. 1, exposing more of the rod 8 outwardly of the knob 11.

When the projections 14 and 15 are in the slots 16 and 17 and the rod 10 is rotated by means of the knob 11, the piston 3 moves axially of the cylinder 1. As the back pressure of the fluid being expelled through the nozzle 4 increases the spring means 9 is compressed causing the rod 8 to move to the left relative to rod 10 as viewed in FIG. 1, and when the rod 8 has been suitably calibrated, the pressure applied to the fluid in the syringe can be determined from a reading of the graduation marks 18.

When the spring means 9 is an extension of the threads of the rod 10, it has been found that if such threads, and hence, the turns of the spring means 9, are single flight threads or turns, the rod 10 tends to bow when the turns are compressed by rotating the rod 10 causing binding against the inner wall of the cylinder 1 and an inaccurate indication of the fluid pressure when it is read at the portion 8a of the rod 8. However, it has also been found that when threads, and hence, the turns of the spring means 9, consist of two or more flights, e.g. flights 19 and 20, such binding is eliminated, or substantially eliminated, with fluid pressures normally encountered.

While is is preferred that the spring means 9 be an extension of the threads on the rod 10 so that the spring means 9 and the piston 3 will be carried by the rod, and so that the turns of the spring means 9 can be engaged with the threads of the collar 13 to propel the piston 3, thereby keeping the length of the cylinder 1 to a minimum and the stroke of the piston 3 to a maximum, it will be apparent that the spring means 9 can be a separate spring of non-corrosive material inserted between the rod 10 and the piston 3, the separate spring preferably being secured at one end to the rod 10 and at its opposite end to the indicator rod 8 or the piston 3. In the latter case, the connection between the separate spring and the rod 10 or the connection between the separate spring and the rod 8 or the piston 3, or both connections, preferably are such that the rod 10 can be rotated without rotating the separate spring or without rotating the piston 3.

The method of using the syringe of the invention is as described in said application Ser. No. 061,642 and as described herein. Thus, the rod 10 and the parts secured thereto, i.e. the spring means 9, the indicator rod 8 and the piston 3 can be withdrawn in the cylinder 1 from nozzle 4 by rotating the collar 13 until the projections 14 and 15 are out of the slots 16 and 17 at which time the rod 10 and said parts can be pulled back in the cylinder 1 to draw fluid into the cylinder 1 through opening 5. The collar 13 is then rotated down rod 10 until the projections 14 and 15 are received in the slots 16 and 17. Thereafter, the rod 10 is rotated by means of the knob 11, causing the piston 3 to move to the right, as viewed in FIG. 1, and the pressure applied to the fluid in the cylinder 1 is indicated by the length 8a of the rod 8 extending outwardly of the knob 11.

The invention is especially useful with syringes of the type described which use a threaded rod with its threads in engagement with threads in fixed relation to the fluid containing cylinder to apply pressure to the fluid because the pressure can reach a relatively high value and the pressure can be controlled precisely. However, the principles of the invention are also applicable to other types of syringes in which the piston is pushed along the cylinder in other ways to apply pressure to the fluid. For example, the threads on the rod 10 and the collar 13 could be omitted, and the rod 10 could be merely manually pushed into the cylinder 1 with the pressure applied to the fluid being indicated by the rod 8.

Although it is preferred that the indicator rod 8 extends outwardly from the knob 11 to provide the indication of pressure because graduations thereon are more readily visible, it will be apparent that it is not necessary that the rod 8 so extend if graduations thereon can be otherwise seen and related to the rod 10, for example, if the knob 11 and/or the rod 10 is transparent so that the graduations on the rod 8 can be seen therethrough.

Although preferred embodiments of the present invention have been described and illustrated, it will be apparent to those skilled in the art that various modifications can be made without departing from the principles of the invention.

We claim:

1. A manually actuable syringe comprising:
   a hollow body with an interior wall, a fluid transport opening at one end thereof and a piston receiving opening at the opposite end thereof;
   a piston within said body which has fluid tight engagement with said interior wall, said piston being slidable toward and away from said transport opening;
   a manually operable actuating rod extending at one end from said piston receiving opening and slidable within said body, said rod having an axial bore;
   compressible spring means interconnecting said piston and the end of said actuating rod nearest said piston; and
   an indicator rod connected at one end to said piston for movement therewith and slidably mounted in said bore of said actuating rod with a portion thereof visible from exteriorly of said body, whereby the position of said portion of said indicator rod is dependent on the position of said piston and the compression of said compressible spring means and indicates the pressure applied by the piston to a fluid within said body.

2. A syringe as set forth in claim 1 wherein said actuating rod is a threaded rod and further comprising:
   a collar mounted on said threaded rod, said collar having a threaded portion mating with the threads on said threaded rod and said collar and said threaded rod being rotatable relative to each other to cause relative movement of said collar and said threaded rod in a direction longitudinally of said rod; and
   co-operating and interengaging means of said body and said collar for releasably securing said collar to said body and thereby preventing movement of said collar in a direction extending from one end to the other of said body, whereby rotation of said threaded rod causes said piston to move in said direction.

3. A syringe as set forth in claim 2 wherein said spring means is integral with said threaded rod and comprises resilient spring turns which are an extension of the threads on said threaded rod, said turns being free to move with respect to each other in the direction axially of said threaded rod.

4. A syringe as set forth in claim 3 wherein the threads on said threaded rod are multiple flight threads and wherein the turns of said spring means are extensions of each of the threads on the threaded rod.

5. A syringe as set forth in claim 1 or 2 wherein the end of said indicator rod opposite from the end thereof which is connected to said piston extends outwardly from said actuating rod and has graduation marks thereon.

6. A syringe as set forth in claim 1, 2 or 3 wherein said piston is made of a flexible, resilient material and is rotatably secured to said spring means to permit rotation of said rod without rotation of said piston.

7. A syringe as set forth in claim 2 wherein said cooperating and interegaging means comprises a pair of spaced projections on said body adjacent said opposite end thereof which extend radially outwardly from said body and which are spaced from each other circumferentially of the body, said projections having a circumferential length less than one-half of the circumference of said body, and said collar has slots therein for receiving said projections, said projections engaging walls of said slots when said collar is adjacent said opposite end and is rotated through a partial turn, and stop means on said collar engageable with at least one of said projections for limiting rotation of said collar.

8. A syringe as set forth in claim 8 wherein said stop means comprises means projecting into an end portion of at least one of said slots.

* * * * *